US005867267A

United States Patent [19]
Benech et al.

[11] Patent Number: 5,867,267
[45] Date of Patent: Feb. 2, 1999

[54] INTERFEROMETRIC DEVICE FOR DETECTION

[75] Inventors: Pierre Benech; Hakon Helmers, both of Grenoble, France

[73] Assignee: Schneider Electric SA, France

[21] Appl. No.: 875,040

[22] PCT Filed: Jan. 29, 1996

[86] PCT No.: PCT/FR96/00145

§ 371 Date: Jul. 17, 1997

§ 102(e) Date: Jul. 17, 1997

[87] PCT Pub. No.: WO96/25656

PCT Pub. Date: Aug. 22, 1996

[30] Foreign Application Priority Data

Feb. 15, 1995 [FR] France ................................. 95/01817

[51] Int. Cl.[6] .................................................. G01B 9/02
[52] U.S. Cl. .......................... 356/345; 356/361; 356/352
[58] Field of Search ................................... 356/345, 352, 356/361; 385/12, 14, 15

[56] References Cited

U.S. PATENT DOCUMENTS 5,692,076  11/1997  DeLisle ....................................... 385/15

FOREIGN PATENT DOCUMENTS

WO92/20990  11/1992  WIPO .
WO93/20430  10/1993  WIPO .

OTHER PUBLICATIONS

Applied Optics, "New integrated–Optics Interferometer in Planar Technology", Sep. 1994, by Duport et al., pp. 5954–5958.
Sensors and Actuators, "Integrated Optical Gas Sensors Using Organically Modified Silicates as Sensitive Films", 1993, by Brandenburg et al., pp. 361–374.
Chemical and Mezcal Sensors, "Gas Sensor Based on an Integrated Optical Interferometer", by Brandenburg et al., pp. 148, 149 & 155.

*Primary Examiner*—Robert Kim
*Attorney, Agent, or Firm*—Parkhurst & Wendel

[57] ABSTRACT

The device comprises a parallel input microguide (2) and output microguide (5) between which a flat guide is arranged forming a transition zone (10). Coupling between the flat guide and the microguides is achieved by an optical tunnel effect. The transition zone comprises at least two zones, a reference zone (10a) and an interaction zone (10b). The interaction zone (10b) is formed by depositing a superstrate whose optical coefficient, or thickness, is sensitive to the medium to be studied. The light beam transmitted by the input microguide to the flat guide is divided into a reference beam passing through the reference zone (10a) and a measurement beam passing through the interaction zone (10b). The measurement and reference beams interfere in the output microguide (5). Depending on the geometrical shape of the reference and interaction zones, the device constitutes a double wave or a multiple wave interferometer. Such a device is used to achieve sensors for applications in physics, chemistry and biology.

9 Claims, 4 Drawing Sheets

INTERFEROMETRIC DEVICE FOR DETECTION

The invention relates to a device for detection of a characteristic of a medium by interferometry, manufactured in integrated optics technology and comprising, on a substrate, an input microguide connected by an input end to means for emitting a light beam, forming means to form at least one reference beam and one measurement beam from said light beam, means for making the reference beam and measurement beam interfere and supply interference signals, means for detection connected to an output end of an output microguide transmitting the interference signals, and an interaction zone between the measurement beam and the medium to be studied.

It is known to use an optic interferometer to detect the presence or concentration of a gas. A known device using an interferometer of the Mach-Zehnder type, achieved in integrated optics technology, is represented in FIG. 1. The interferometer comprises a substrate 1 on which an input microguide 2 is achieved. The input microguide 2 is divided into two arms by a first Y-junction, a reference arm 3 and a measurement arm 4. The two arms are joined, by means of a second Y-junction, in an output microguide 5. An interaction zone 6 with the gas to be studied covers a part of the measurement arm 4. This interaction zone is for example covered by a film able to absorb a predetermined gas and whose refraction coefficient changes according to the quantity of gas absorbed. An input light beam 7 applied to the input of the microguide 2 is therefore separated into two beams one of which is transmitted by the reference arm to the output microguide and the other of which, transmitted by the measurement arm, undergoes a variable phase displacement according to the variation of the coefficient of the absorbent film. The reference and measurement beams interfere in the second Y-junction and the interference signal thus formed detected at the output of the microguide 5 is representative of the gas to be studied.

The object of the invention is to achieve a device presenting an increased sensitivity while being easy to achieve in integrated optics.

According to the invention, this object is achieved by the fact that the forming means comprise a flat guide arranged between the input and output microguides in such a way as to achieve light coupling by optical tunnel effect between each microguide and the flat guide, and comprising at least a first zone, not sensitive to the medium, and a second zone constituting the interaction zone with the medium. The different zones can be of any shape.

The flat guide is bounded by two sides respectively parallel to the input and output microguides, each of said sides being arranged near to an intermediate part of an associated microguide.

According to a development of the invention, the interaction zone comprises a superstrate sensitive to the medium to be studied and deposited on the substrate.

According to a first alternative embodiment, the input and output microguides are parallel and the interaction zone has the shape of a parallelogram having two sides parallel to the microguides.

According to a second alternative embodiment, the interaction zone has the shape of a triangle having one side on the same side as the flat guide associated to the input microguide and an opposite peak on the same side as the flat guide associated to the output microguide.

Other advantages and features of the invention will become more clearly apparent from the following description of particular embodiments of the invention, given as non-restrictive examples only and represented in the accompanying drawings in which.

Figure 2:
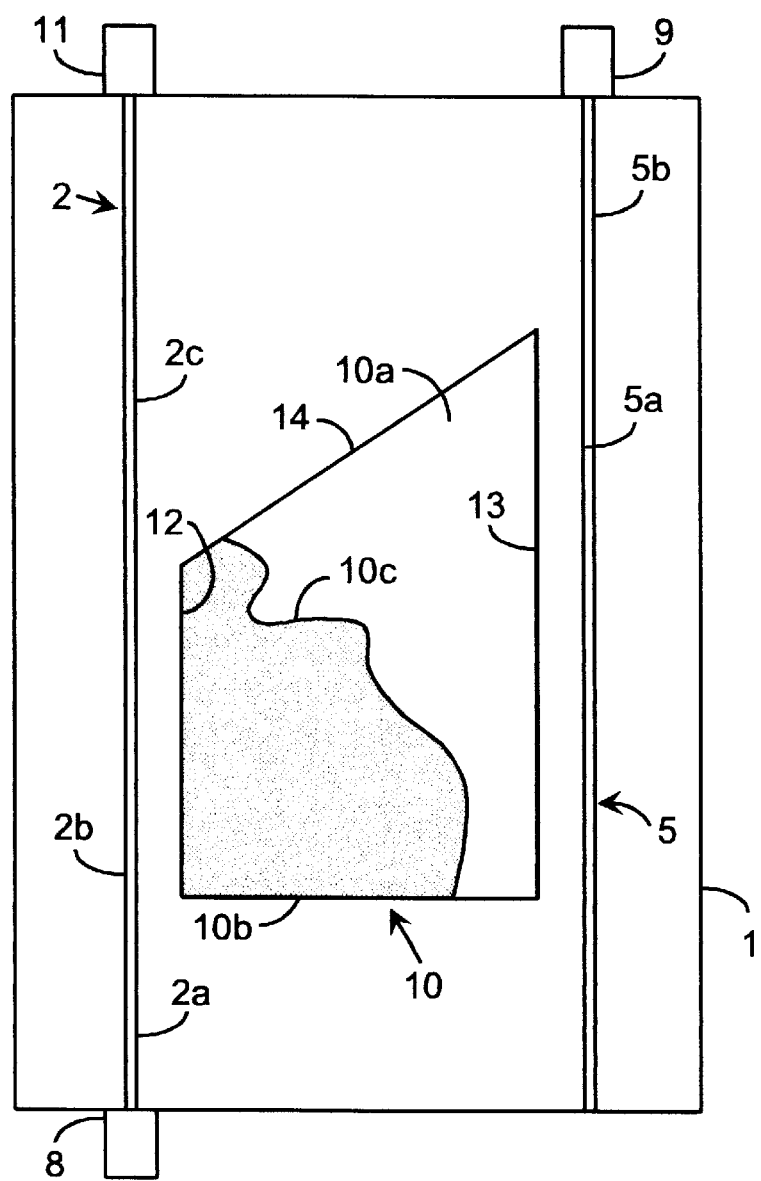
FIG. 2 represents an embodiment of the device according to the invention.

The device according to FIG. 2 is achieved in integrated optics technology on a substrate 1. As in known devices, an input end of an input microguide 2 is connected to a light source 8. Such a source can be formed by a laser diode fixed directly onto the substrate 1 or be connected to the input of the microguide 2 by means of an optical fibre. The output end of the output microguide 5 is connected to a photodetector 9. The microguides 2 and 5 are preferably appreciably parallel and a transition zone formed by a flat guide 10 is arranged between the microguides 2 and 5 in such a way as to achieve coupling of the light by optical tunnel effect, also called frustrated total reflection, between the input microguide 2 and the flat guide 10 and between the flat guide 10 and the output microguide 5.

A first, input, part 2a of the microguide 2, connected to the source 8, serves the purpose of stabilising the fundamental mode of the microguide. Then, in a second, intermediate, part 2b of the microguide 2 located near the transition zone 10, the light is coupled by optical tunnel effect in the zone 10. The coupling is relatively weak, thus ensuring a regular light distribution in the zone 10. The non-coupled part of the light is output from the device via a third, output, part 2c of the microguide 2. A reference photodetector 11 is connected to the output of the microguide 2. The reference signal thus measured can be used in a processing unit to correct the variations in the measurement of the interference signal performed by the photodetector 9 due to variations of the source 8.

The transition zone 10 is divided into at least two zones 10a and 10b. A first zone 10a acts as reference zone. The second zone 10b constitutes an interaction zone with the medium to be studied. It is covered by a superstrate whose optical coefficient and/or thickness is modified when it interacts with the above-mentioned medium. This modification gives rise to a modification of the propagation constant of the optical wave in the optical medium constituted by the part of the flat guide located below the superstrate.

The light which has passed through the zone 10 is coupled by optical tunnel effect with an intermediate part 5a of the output microguide, located nearby. The part 5a thus forms a coupling and interference zone in which interference signals form constituted by the sum of the light rays coming from the part 2b and having passed respectively through the zones 10a and 10b. There is therefore interference between the reference light beams having passed through the reference zone 10a and measurement light beams, displaced according to the composition of the medium to be studied. This is particularly illustrated in FIG. 3 where a few light rays are represented. The interference signals are transmitted to the photodetector 9 by an output part 5b of the microguide 5.

The reference zone 10a and interaction zone 10b may have any geometrical shape. In FIG. 2, they are separated by a line 10c of totally arbitrary shape. According to a preferred embodiment represented in FIG. 2, the transition zone 10 is trapezoid. It comprises a small base 12 near to the part 2b and parallel to the latter and a large base 13 near to the part 5a of the output microguide 5. In FIG. 2 it has the shape of a rectangular trapezoid whose inclined side 14 is arranged on the same side as the output ends of the microguides 2 and 5.

Such a device is very simple to achieve and easily reproducible. A standard basic device comprises the microguides 2 and 5 and the flat guide 10 and possibly the source 8 and photodetectors 9 and 11. Such a device can be manufactured in series and be adapted to suit requirements by simply depositing a superstrate suited to the medium to be studied and whose geometrical shape is chosen arbitrarily. The reference zone 10a can if required also be covered by any material not sensitive to the medium to be studied.

Figure 3:
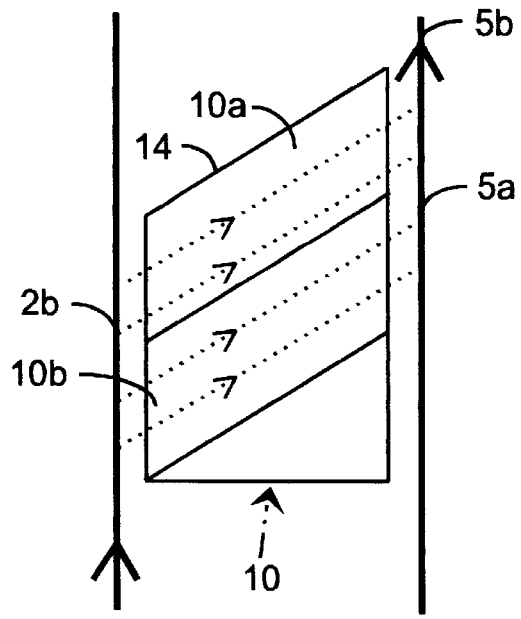
FIGS. 3 and 4 represent two particular embodiments of the flat guide of the device according to FIG. 2, in a double wave interferometer.
Figure 4:
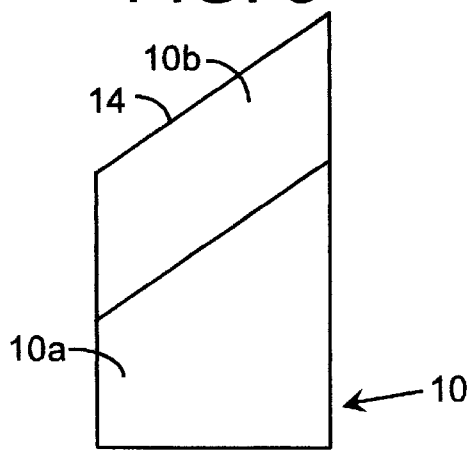

In the alternative embodiments of FIGS. 3 and 4, the interaction zone 10b has the shape of a parallelogram having two sides situated respectively on the small base 12 and on the large base 13 of the rectangular trapezoid constituting the transition zone. In FIG. 3, the interaction zone is arranged in the centre part of the zone 10. The reference zone 10a is then formed by the remainder of the zone 10 located above the zone 10b. In FIG. 4, the zone 10b is arranged in the upper part of the zone 10. In both cases the interferometer thus formed is a double wave interferometer whose response curve is of the form represented in FIG. 5. The curve represents the intensity | of the interference signals with respect to the phase displacement Ø, introduced by the interaction zone 10b, between the measurement and reference beams. Such a curve has the following form:

$$|=|o\ (1+\cos\emptyset) \quad (1)$$

where |o is the intensity of the signals in the absence of phase displacement. The phase displacement Ø can be proportional to the refraction coefficient n of the superstrate deposited on the interaction zone 10b, variable according to the medium to be studied. A response of this type is suitable for large measurement ranges. The width of the interaction zone 10b with respect to the reference zone 10a decides the distribution of the light intensity between these two zones, which enables the contrast of the interferometer to be optimised.

Figure 6:
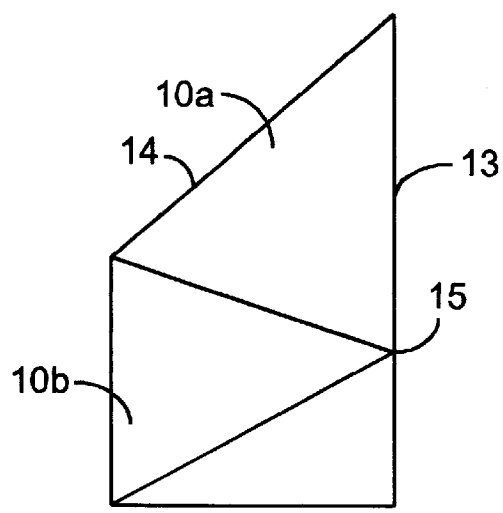
FIGS. 6, 7 and 9 represent three particular embodiments of the flat guide of the device according to FIG. 2, in a multiple wave interferometer.
Figure 7:
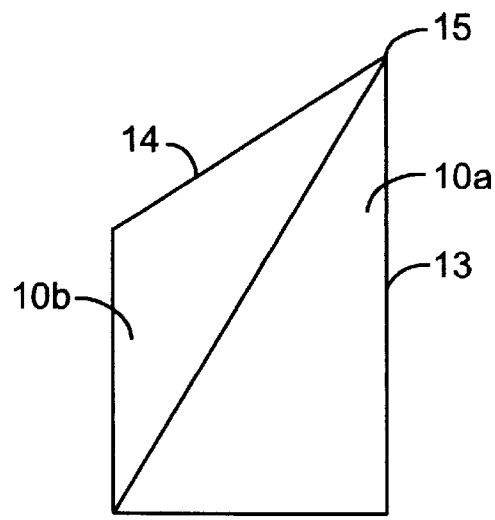
Figure 9:
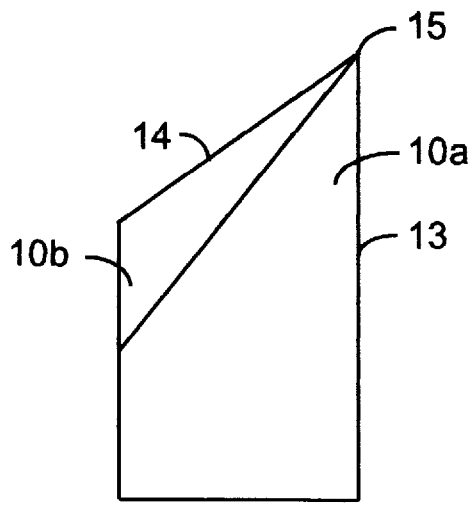

In the alternative embodiments of FIGS. 6, 7 and 9, the interaction zone 10b has the shape of a triangle one side of which is situated on the small base 12 of the trapezoid and whose opposite peak 15 is situated on the large base 13 of the trapezoid. In FIGS. 6 and 7, the above-mentioned side of the triangle has the same length as the small base 12 whereas in FIG. 9 said side is smaller than the small base 12. In FIG. 6, the peak 15 is situated in the middle part of the large base 13. In FIGS. 7 and 9, a second side of the triangle is situated identically with the inclined side 14 of the trapezoid.

Figure 8:
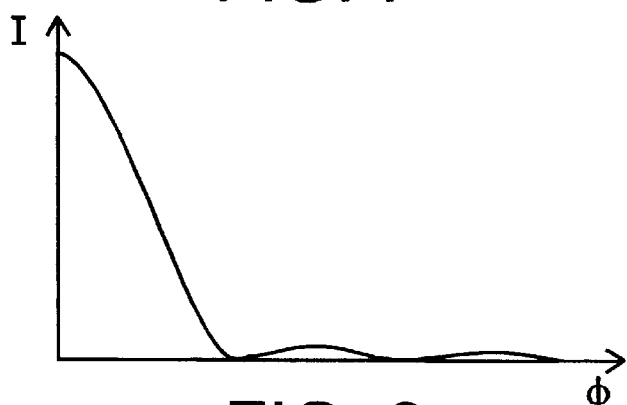
FIGS. 8 and 10 illustrate respectively the amplitude-phase displacement response curves of the devices according to FIGS. 7 and 9.

The response curve of the embodiments of FIGS. 6 and 7, represented in FIG. 8, has the form:

$$|=|o\ (1-\cos\emptyset)/\emptyset^2 \quad (2)$$

This response is more particularly suited to unambiguous level detection, a predetermined intensity level corresponding to a given phase displacement level, when above the level of the oscillations.

Figure 5:
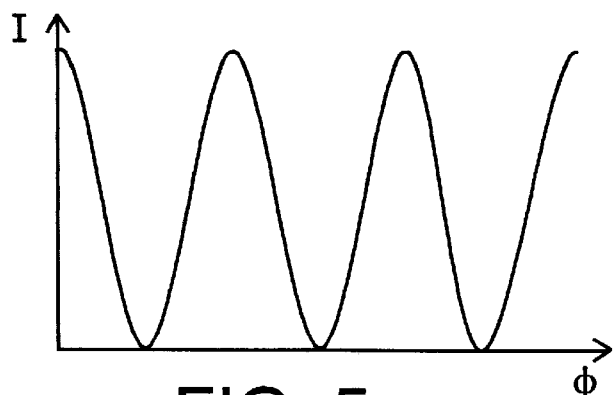
FIG. 5 illustrates the amplitude-phase displacement response curve of the devices according to FIGS. 3 and 4.
Figure 10:
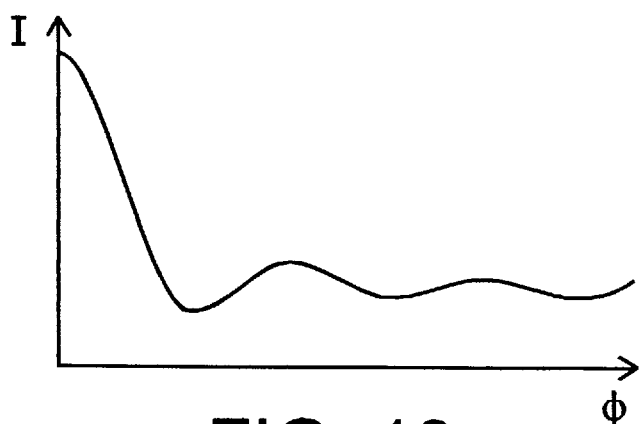

FIG. 10 represents the response curve of the alternative embodiment of FIG. 9, which is an intermediate response between those of FIGS. 5 and 8.

In the three embodiments of FIGS. 6, 7 and 9, the interferometer thus formed is a multiple wave interferometer.

The invention is not limited to the particular geometrical shapes represented in the figures but extends to any geometrical shape of the transition zone and of the lines separating the interaction zone 10b and the reference zone 10a. The zone 10 can in particular be divided into several sensitive zones and into several reference zones.

The amplitude-phase displacement response of the interferometer is therefore determined by the geometrical shape of the layers deposited on the substrate of the device. It can be of the same type as that of a resonator, of a double wave interferometer, or of any other intermediate response.

Figure 1:
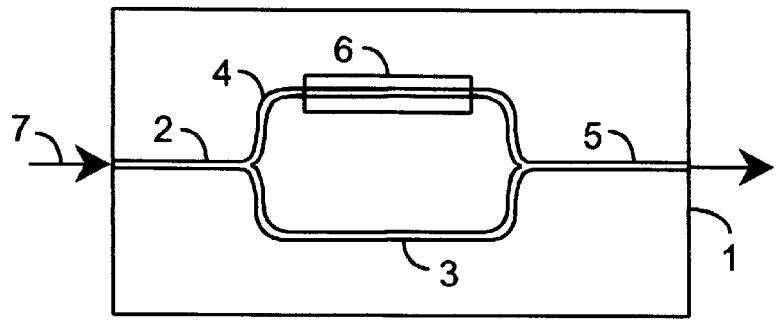
FIG. 1 represents a device of known type.

In a double wave interferometer of known type, as represented in FIG. 1, depositing an absorbent substrate on the interaction zone 6 may unbalance the arms of the interferometer, which has a harmful effect on the contrast of the measurement signal. With a device according to the invention, free choice of the interaction zone geometry enables this problem to be avoided.

Moreover, the interaction surface 10b may be large, which reduces the sensitivity of the interferometer to any possible non-homogeneities of the substrate covering the interaction zone.

Furthermore, the device according to the invention does not, unlike known Fabry-Pérot type interferometers, comprise reflecting elements which are delicate to achieve in integrated optics. Neither does it comprise curved guides, unlike the known device according to FIG. 1, which guides cause problems in certain integrated optics technologies. This results in a simplicity of manufacture which can lead to a substantial reduction of the production cost of a sensor of this type.

The device naturally also presents all the advantages inherent to integrated optics, notably insensitivity to vibrations, compactness, easy temperature control, possibility of manufacture in series and resistance to electromagnetic disturbances.

The device described above can be used to achieve sensors for applications in physics, chemistry or biology, the medium to be studied coming into contact with the superstrate deposited on the interaction zone. More generally it can be used each time an interaction is to be established between an external medium and light.

We claim:

1. A device for detection of a characteristic of a medium by interferometry, manufactured in integrated optics technology and comprising, on a substrate (1), an input microguide (2) connected by an input end to means (8) for emitting a light beam, forming means (10a, 10b) to form at least one reference beam and one measurement beam from said light beam, means (5a) for making the reference beam and measurement beam interfere and supply interference signals, means (9) for detection connected to an output end of an output microguide (5) transmitting the interference signals, and an interaction zone (10b) between the measurement beam and the medium to be studied, a device characterized in that the forming means comprise a flat guide (10) arranged between the input and output microguides (2, 5) in such a way as to achieve light coupling by optical tunnel effect between each microguide and the flat guide, and comprising at least a first zone (10a), not sensitive to the medium, and a second zone (10b) constituting the interaction zone with the medium.

2. The device according to claim 1, characterized in that the interaction zone comprises a superstrate sensitive to the medium to be studied and deposited on the substrate (1).

3. The device according to claim 2, characterized in that the optical coefficient of the superstrate varies according to the characteristic of the medium to be studied.

4. The device according to claim 2, characterized in that the thickness of the superstrate varies according to the characteristic of the medium to be studied.

5. The device according to claim 1, characterized in that the flat guide (10) is bounded by two sides (12, 13) respectively parallel to the input and output microguides (2, 5), each of said sides being arranged near to an intermediate part (2b, 5a) of an associated microguide.

6. The device according to claim 5, characterized in that the side (13) of the flat guide associated to the output microguide (5) is longer than the side (12) of the flat guide associated to the input microguide (2).

7. The device according to claim 5, characterized in that the input and output microguides (2, 5) are parallel and that the interaction zone (10b) has the shape of a parallelogram having two sides parallel to the microguides (2, 5).

8. The device according to claim 5, characterized in that the interaction zone (10b) has the shape of a triangle having one side on the same side (12) as the flat guide (10) associated to the input microguide (2) and an opposite peak (15) on the same side (13) as the flat guide (10) associated to the output microguide (5).

9. The device according to claim 1, characterized in that it comprises means (11) for detecting a reference light signal connected to an output end of the input microguide (2).

* * * * *